United States Patent
Chen

(10) Patent No.: US 10,261,346 B2
(45) Date of Patent: Apr. 16, 2019

(54) EYE GLASSES STRUCTURE

(71) Applicant: Lin Yun Chen, Tainan (TW)

(72) Inventor: Lin Yun Chen, Tainan (TW)

(*) Notice: Subject to any disclaimer, the term of this patent is extended or adjusted under 35 U.S.C. 154(b) by 0 days.

(21) Appl. No.: 15/632,384

(22) Filed: Jun. 25, 2017

(65) Prior Publication Data

US 2018/0373064 A1    Dec. 27, 2018

(51) Int. Cl.
*G02C 11/00* (2006.01)
*G02C 1/00* (2006.01)
*G02C 9/04* (2006.01)
*G02C 11/04* (2006.01)

(52) U.S. Cl.
CPC .............. *G02C 11/10* (2013.01); *G02C 1/10* (2013.01); *G02C 9/04* (2013.01); *G02C 11/04* (2013.01); *G02C 2200/06* (2013.01)

(58) Field of Classification Search
CPC ............ G02C 9/04; G02C 11/10; G02C 11/04
USPC ...................... 351/51, 52, 123, 158
See application file for complete search history.

(56) References Cited

U.S. PATENT DOCUMENTS

2012/0262667 A1* 10/2012 Willey .................. G02C 7/083
                                                                         351/158
2015/0290039 A1* 10/2015 McCulloch ............ A61F 9/029
                                                                         2/439

* cited by examiner

*Primary Examiner* — Darryl J Collins
(74) *Attorney, Agent, or Firm* — Bruce Stone LLP; Joseph Bruce

(57) ABSTRACT

Provided is an eyeglasses structure, including a mounting groove provided inside at least one side of a frame, wherein the mounting groove has a perforation inside. When an electronic device passes through the perforation, the electronic device is fastened to the mounting groove. In addition, the electronic device has a switch that is exposed to the mounting groove.

5 Claims, 5 Drawing Sheets

EYE GLASSES STRUCTURE

BACKGROUND OF THE INVENTION

1. Field of the Invention

The present disclosure relates to a pair of glasses, and particularly relates to an eyeglasses structure which has a mounting groove.

2. The Prior Arts

In general, people wear a pair of glasses for myopia or have special needs to wear a pair of glasses. However, the current glasses products have been diversified and fashionable. Although the current glasses can be divided into two categories: corrective glasses and protective glasses. The protective glasses have become increasingly important, for example, the protective glasses are able to protect a user's eyes from the strong sun light and ultraviolet or are suitable for industrial environments to prevent foreign objects from flying into the eyes. Therefore, the glasses have become an indispensable thing in today's life.

Specifically, with the progress of science and technology and the continuous improvement of quality of life, a variety of different uses of glasses came into being. However, special-purpose glasses can only be applied to special-purpose environments, and the quality requirements of the protective glasses are getting higher and higher.

Accordingly, in addition to the general use of glasses, the glasses can also be applied to a variety of different working environments. For example, when a user operates a grinder or a machine and also dozes off at the same time, how to provide a better eyeglasses structure in order to remind the user to avoid being caught when operating a grinder or a machine is one of the important issues.

SUMMARY OF THE INVENTION

It is a primary object of the present invention to provide an eyeglasses structure.

In order to achieve the above objective, the present disclosure provides an eyeglasses structure, including a mounting groove that is provided inside at least one side of a frame, wherein the mounting groove has a perforation inside. When an electronic passes through the perforation, the electronic is fastened to the mounting groove. The electronic device has a switch that is exposed to the mounting groove.

Preferably, the electronic device is one of a video camera, a camera, an ultraviolet detecting device, a gas/biogas detecting device, a doze detecting device and a lighting device.

Preferably, the electronic device is suitable for water, snow, desert, alpine terrain or high altitude.

Preferably, the outer ends of two sides of the frame have a connecting member to connect with a belt.

Preferably, the outer ends of two sides of the frame have a connecting member to connect with a temple.

DETAILED DESCRIPTION OF THE PREFERRED EMBODIMENT

The detailed description of the present invention is provided in combination with the accompanying drawings.

Figure 1:
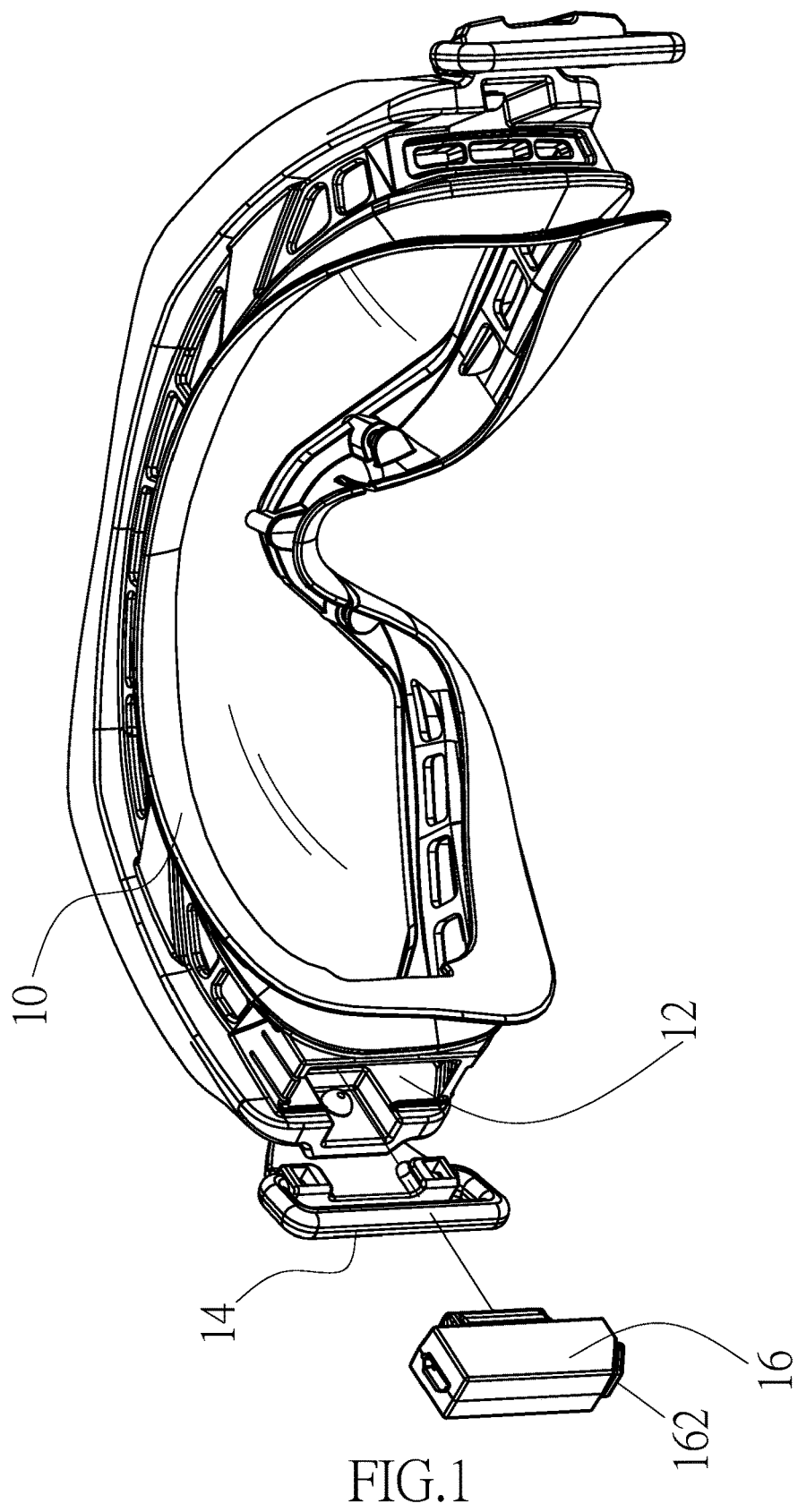
FIG. 1 shows a three-dimensional diagram of an eyeglasses structure having a mounting groove according to a preferred embodiment of the present disclosure.

As shown in FIG. 1, an eyeglasses structure of the present disclosure includes a frame 10, a mounting groove 12 and a connecting member 14.

Figure 3:
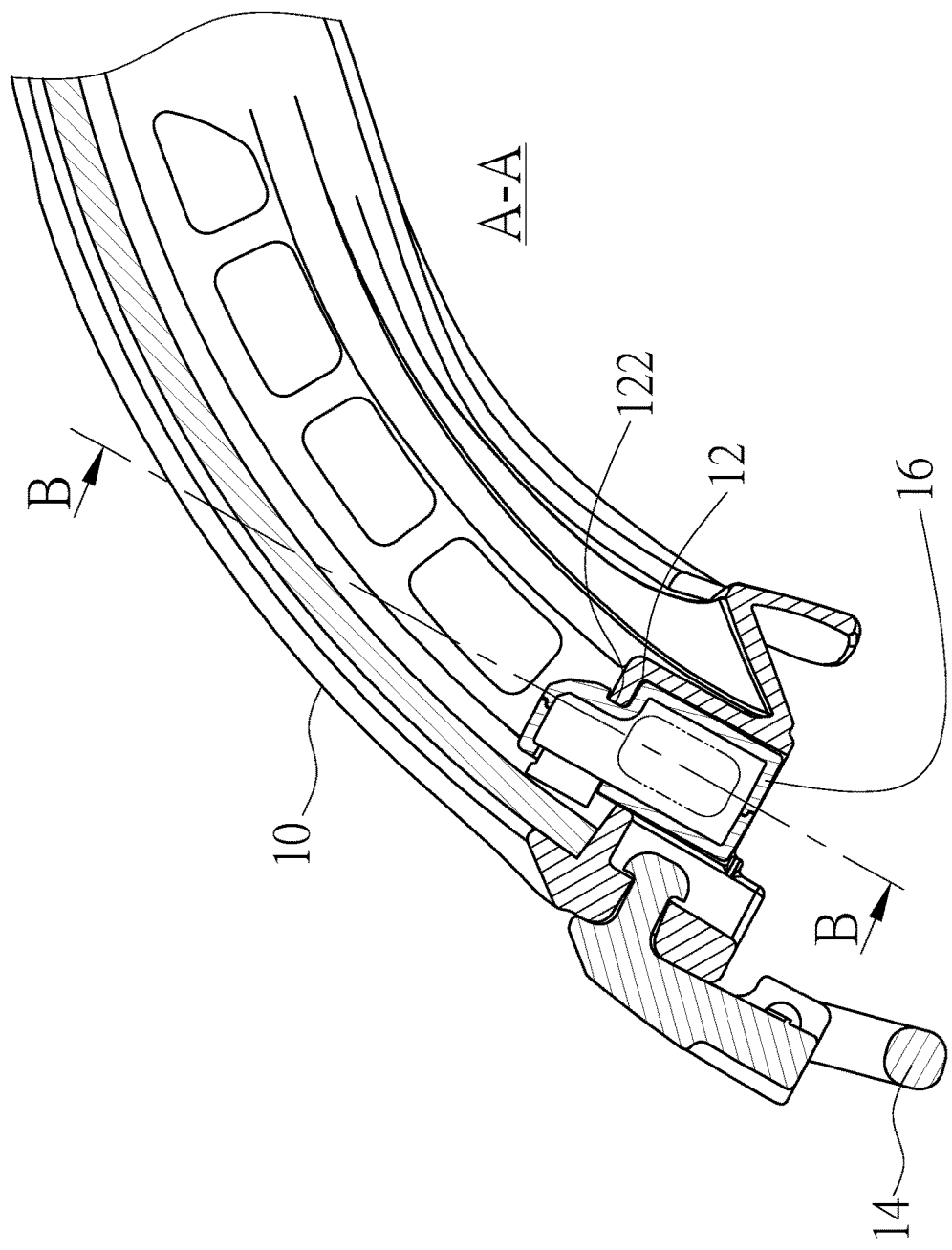
FIG. 3 shows a cross-sectional view taken along lines A-A of FIG. 2 according to a preferred embodiment of the present disclosure.

Referring to FIG. 1, the mounting groove 12 of the present disclosure is provided inside at least one side of the frame 10. The mounting groove 12 has a perforation 122 (as shown in FIG. 3) inside. When an electronic device 16 passes through the perforation 122, the electronic device 16 is fastened to the mounting groove 12. In addition, the electronic device 16 has a switch 162. The switch 162 is exposed to the mounting groove 12 so as to turn on and off the electronic device 16.

Moreover, as shown in FIG. 1, the electronic device 16 of the present disclosure may be one of a video camera, a camera, an ultraviolet detecting device, a gas/biogas detecting device, a doze detecting device and a lighting device.

Specifically, if a video camera is installed inside the eyeglasses structure of the present disclosure, dynamic videos or static shooting can be carried out. If a camera is installed inside the eyeglasses structure of the present disclosure, images can be shot or recorded. If a user needs to wear a pair glasses to work on the construction, gas/biogas devices can be installed inside the eyeglasses structure of the present disclosure. When the gas/biogas devices detect the toxic gas, a warning sign can be provided immediately. If a user is often exposed to ultraviolet generated by industrial equipment, and ultraviolet will cause eye surface tissue damage or cause skin sunburn, pain, etc., the ultraviolet detecting device can be installed inside the eyeglasses structure of the present disclosure so as to provide a warning sign immediately. In addition, if a user dozes off at work, a doze detecting device can immediately remind the user to avoid being caught when operating a grinder or a machine. Further, the lighting device can be installed inside the eyeglasses structure of the present disclosure to provide enough lighting.

That is to say, as long as a user wears a pair of glasses at work or during exercise, the above functions and technical effects can be achieved by the eyeglasses structure of the present disclosure.

Figure 2:
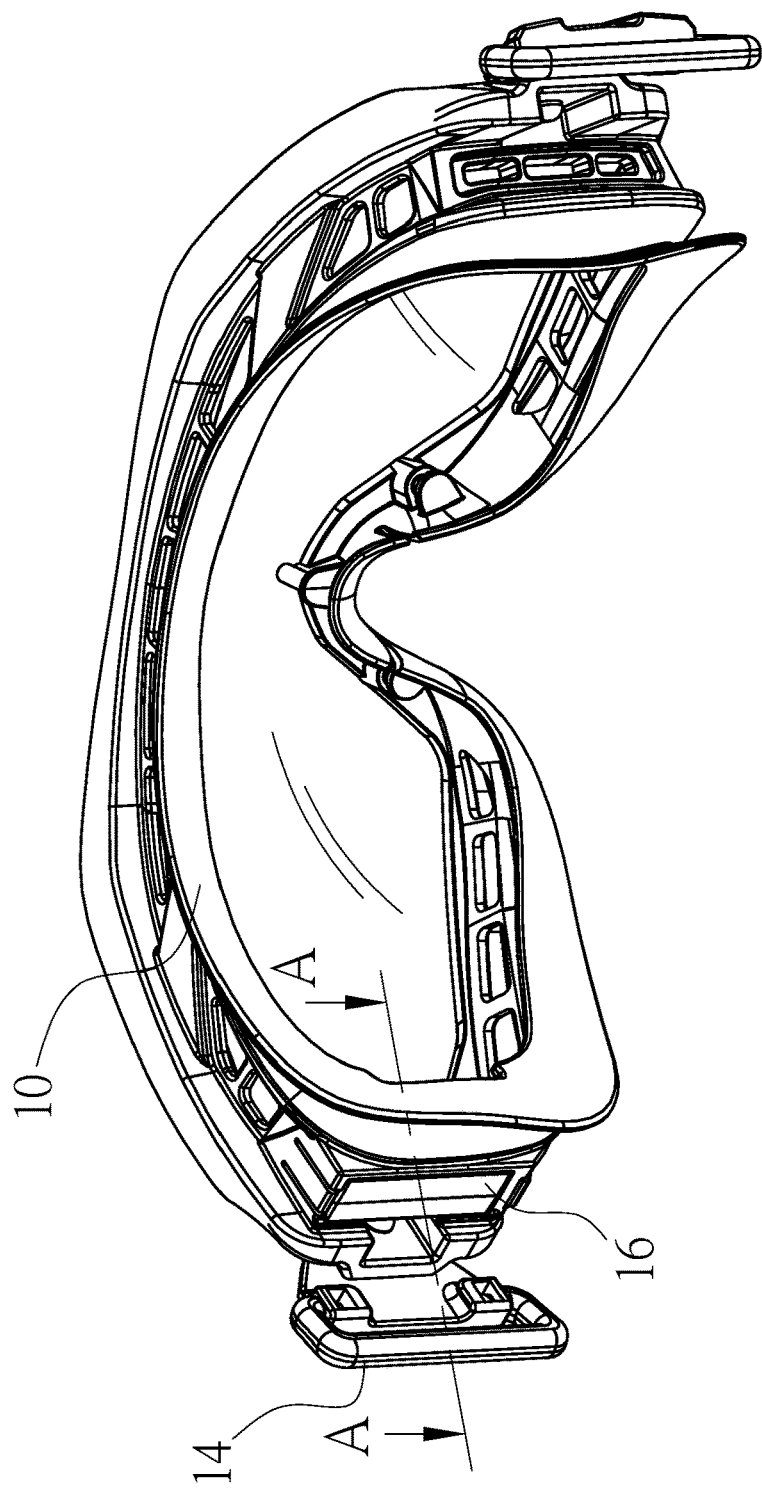
FIG. 2 shows a three-dimensional diagram of an eyeglasses structure that an electronic device is installed inside the mounting groove according to a preferred embodiment of the present disclosure.

As shown in FIGS. 1 and 2, the electronic device 16 installed inside the eyeglasses structure of the present disclosure may be suitable for water, snow, desert, alpine terrain or high altitude. Additionally, the electronic device 16 may also be suitable for different temperature ranges.

Figure 4:
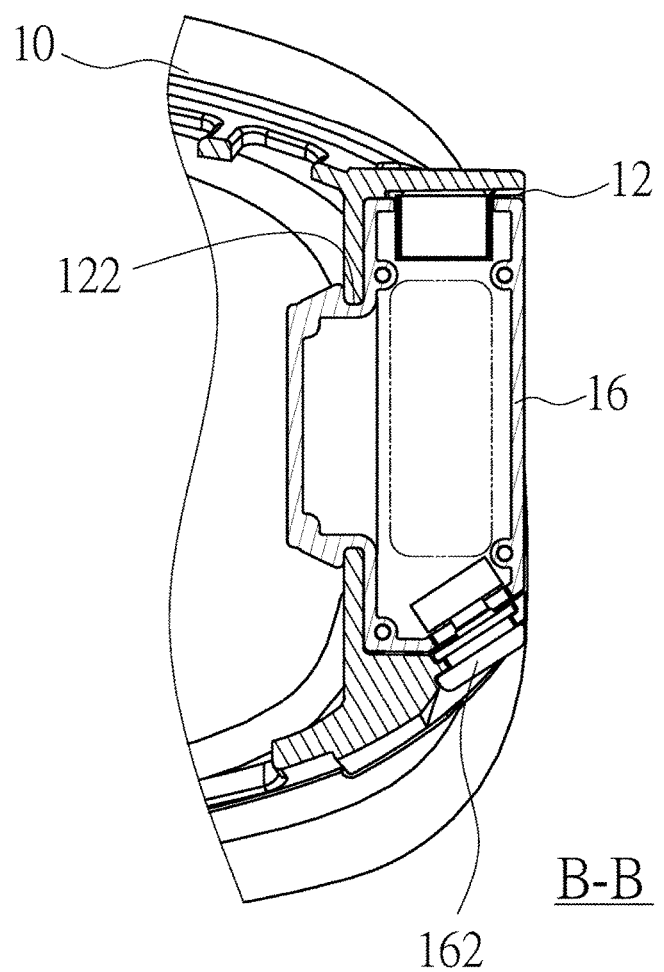
FIG. 4 shows a cross-sectional view taken along lines B-B of FIG. 3 according to a preferred embodiment of the present disclosure.

FIG. 3 shows a cross-sectional view taken along lines A-A of FIG. 2 according to a preferred embodiment of the present disclosure and FIG. 4 shows a cross-sectional view taken along lines B-B of FIG. 3 according to a preferred embodiment of the present disclosure.

It should be noted that the outer ends of two sides of the frame 10 may have a connecting member 14 so as to connect with a belt (not shown) or a temple (not shown), as shown in FIGS. 1 to 3.

Figure 5:
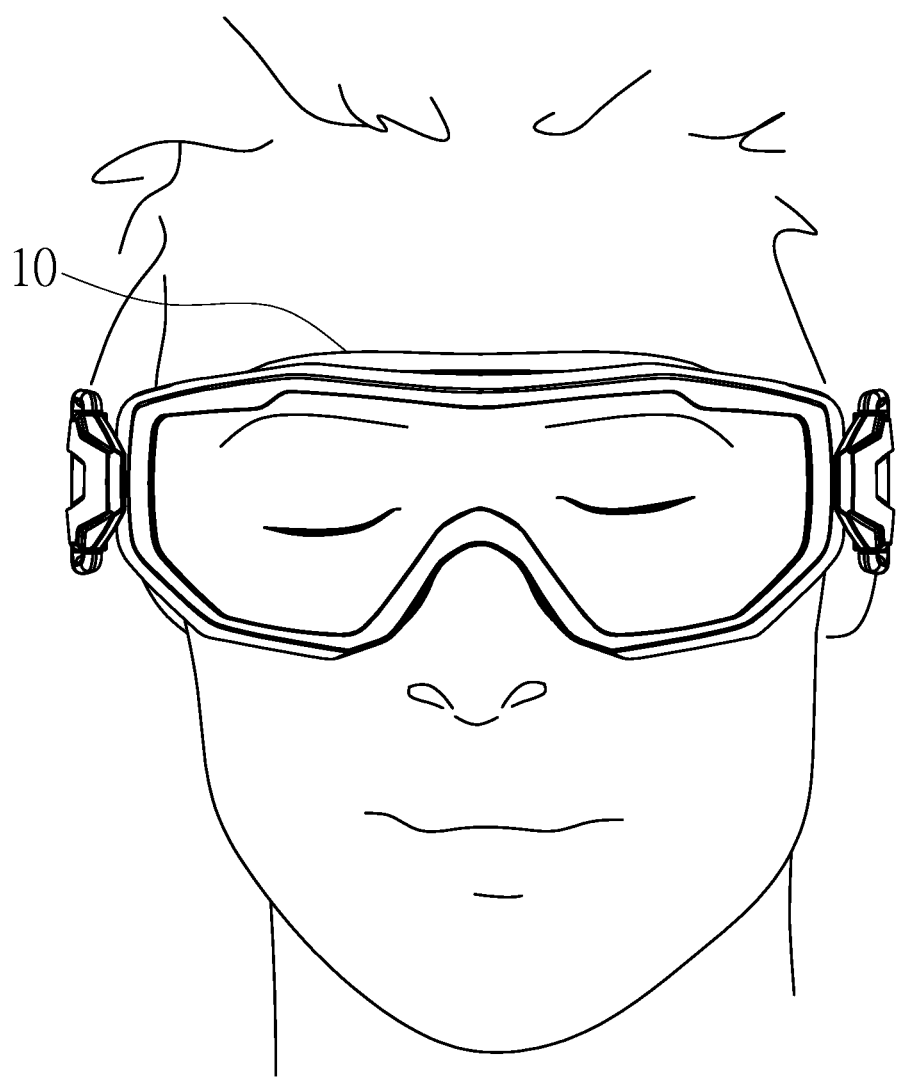
FIG. 5 shows a three-dimensional diagram of an eyeglasses structure immediately issuing a warning when a doze is detected according to a preferred embodiment of the present disclosure.

According to a preferred embodiment of the present disclosure, as shown in FIG. 5, the doze detecting device is installed inside the eyeglasses structure of the present disclosure. When a user wearing the eyeglasses structure of the present disclosure dozes off, the doze detecting device will provide immediate warning (e.g. vibration or sound) to alert the user.

To sum up, according to the electronic device installed inside the eyeglasses structure of the present disclosure, the present disclosure has the following advantages. Since different electronic detecting devices can be installed inside the mounting groove of the present disclosure, the eyeglasses structure of the present disclosure can provide immediate warning (for example, vibration or sound) to alert the user, and thus reducing the incidence of accidental injuries.

Although the present disclosure has been described with reference to the preferred exemplary preferred embodiments thereof, it is apparent to those skilled in the art that a variety of modifications and changes may be made without departing from the scope of the present disclosure which is intended to be defined by the appended claims.

What is claimed is:

1. An eyeglasses structure, comprising:
   a mounting groove provided inside at least one side of a frame,
   wherein the mounting groove has a perforation inside; an electronic device is fastened to the mounting groove by directly passing through the perforation and the electronic device has a switch exposed to the mounting groove.

2. The eyeglasses structure of claim 1, wherein the electronic device is one of a video camera, a camera, an ultraviolet detecting device, a gas/biogas detecting device, a doze detecting device and a lighting device.

3. The eyeglasses structure of claim 1, wherein the electronic device is suitable for water, snow, desert, alpine terrain or high altitude.

4. The eyeglasses structure of claim 1, wherein outer ends of two sides of the frame have a connecting member to connect with a belt.

5. The eyeglasses structure of claim 1, wherein outer ends of two sides of the frame have a connecting member to connect with a temple.

* * * * *